US00PP31540P2

(12) United States Plant Patent
Danziger

(10) Patent No.: US PP31,540 P2
(45) Date of Patent: Mar. 10, 2020

(54) ***PETUNIA* PLANT NAMED 'DAMORPURP'**

(50) Latin Name: ***Petunia* hybrid**
Varietal Denomination: DAMORPURP

(71) Applicant: Gavriel Danziger, Beit Dagan (IL)

(72) Inventor: Gavriel Danziger, Beit Dagan (IL)

(73) Assignee: Danziger 'DAN'Flower Farm (IL)

( * ) Notice: Subject to any disclaimer, the term of this patent is extended or adjusted under 35 U.S.C. 154(b) by 0 days.

(21) Appl. No.: 16/350,026

(22) Filed: Sep. 13, 2018

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824; A01H 5/02
See application file for complete search history.

*Primary Examiner* — Keith O. Robinson
(74) *Attorney, Agent, or Firm* — Cassandra Bright

(57) ABSTRACT

A new and distinct *Petunia* cultivar named 'DAMORPURP' is disclosed, characterized by a semi-trailing growth habit, and large, violet-blue flowers with white stripes. The plants are medium branched with a medium vigor. The new variety is a *Petunia*, normally produced as an outdoor garden or container plant.

2 Drawing Sheets

Figure 1:
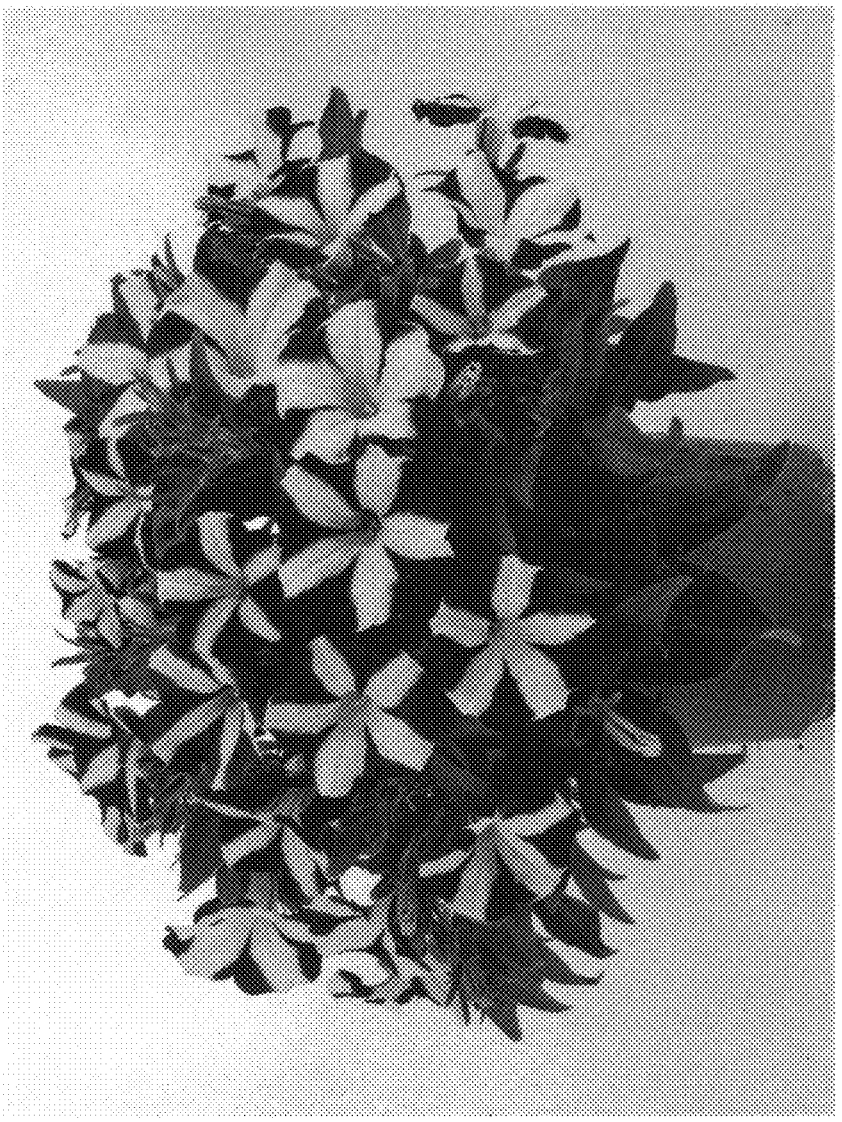

Latin name of the genus and species: *Petunia* hybrid.
Variety denomination: 'DAMORPURP'.

BACKGROUND OF THE INVENTION

The new *Petunia* hybrid cultivar is a product of a planned breeding program conducted by the inventor, Gavriel Danziger in Moshav Mishmar Hashiva, Israel. The objective of the breeding program was to produce new *Petunia* varieties with interesting flower color patterns. The cross resulting in this new variety was made during January of 2015.

The seed parent is the unpatented, propriety variety referred to as *Petunia* 'cv. 14-9229'. The pollen parent is the unpatented, propriety variety referred to as *Petunia* 'cv. 14-9127'. The new variety was discovered in August of 2015 by the inventor in a group of seedlings resulting from the 2015 crossing, in a greenhouse in Moshav Mishmar Hashiva, Israel.

Asexual reproduction of the new cultivar 'DAMORPURP' was first performed by terminal vegetative cuttings during August of 2015, at a greenhouse in Moshav Mishmar Hashiva, Israel. Subsequent propagation has shown that the unique features of this cultivar are stable and reproduced true to type in more than 25 successive generations.

SUMMARY OF THE INVENTION

The cultivar 'DAMORPURP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAMORPURP'. These characteristics in combination distinguish 'DAMORPURP' as a new and distinct *Petunia* cultivar:

1. Mounded growth habit.
2. Very branched with medium vigor.

3. Flowers color is purple-blue with white stripes (light intensity and weather conditions can influence the width of the stripes, creating shapes resembling hearts).
4. Flower size is large.
5. Abundant flowering.

PARENT COMPARISON

Plants of the new cultivar 'DAMORPURP' are similar to plants of the seed parent, *Petunia* 'cv. 14-9229' in most horticultural characteristics, however, plants of the new cultivar 'DAMORPURP' differ in the following;

1. 'Cv. 14-9229' has semi trailing growth habit while 'DAMORPURP' has mounded growth habit.
2. 'Cv. 14-9229' is a branched plant with low vigor while 'DAMORPURP' is very branched with medium vigor.
3. 'Cv. 14-9229' flower color is magenta with white stripes while 'DAMORPURP' flowers color is purple-blue with white stripes.
4. 'Cv. 14-9229' flower size is medium while 'DAMORPURP' flower size is large.
5. 'Cv. 14-9229' has medium quantity of flowering while 'DAMORPURP' has abundant flowering.

Plants of the new cultivar 'DAMORPURP' are similar to plants of the pollen parent in most horticultural characteristics however, plants of the new cultivar 'DAMORPURP' differ in the following;

1. 'Cv-14-9127' has semi upright growth habit and is a tall plant, while 'DAMORPURP' has mounded growth habit.
2. 'Cv-14-9127' is vigorous with low branching, while 'DAMORPURP' is very branched with medium vigor.
3. 'Cv-14-9127' flower color is blue with white stripes while 'DAMORPURP' flowers color is purple-blue with white stripes.
4. 'Cv-14-9127' flower size is medium while 'DAMORPURP' flower size is large.

5. 'Cv-14-9127' has medium quantity of flowering while 'DAMORPURP' has abundant flowering.

COMMERCIAL COMPARISON

Plants of the new cultivar 'DAMORPURP' can be compared to the unpatented commercial variety *Petunia* 'DANCAS305'. These varieties are similar in most horticultural characteristics; however, 'DAMORPURP' differs in the following:

1. 'DANCAS305' flower size is smaller than 'DAMORPURP'.
2. 'DANCAS305' Flower color is red-purple with white stripes, while 'DAMORPURP' has purple-blue flowers with white stripes.
3. 'DANCAS305' plant habit is semi-trailing, while 'DAMORPURP' has a mounded growth habit.

Plants of the new cultivar 'DAMORPURP' can also be compared to the commercial variety *Petunia* 'DRAY67', U.S. Plant Pat. No. 25,906. These varieties are similar in most horticultural characteristics; however, 'DAMORPURP' differs in the following:

1. 'DRAY67' flower size is smaller than 'DAMORPURP'.
2. 'DRAY67' flower color is black with yellow stripes, while 'DAMORPURP' has purple-blue flowers with white stripes.
3. 'DRAY67' is taller than 'DAMORPURP'.

BRIEF DESCRIPTION OF THE PHOTOGRAPHS

The accompanying photograph in FIG. 1 illustrates in full color a typical plant of 'DAMORPURP' grown in a greenhouse, in Moshav Mishmar Hashiva, Israel.

Figure 2:
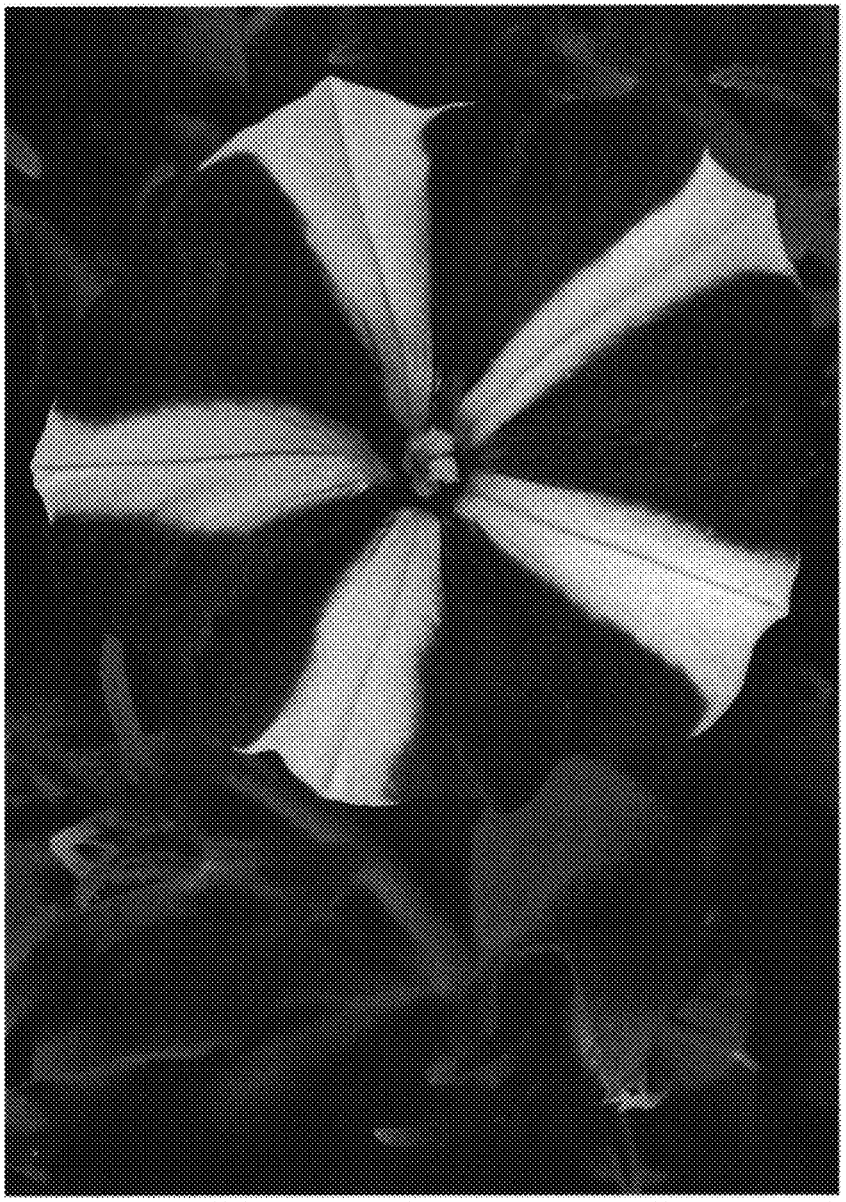

FIG. 2 illustrates in full color a typical mature flower of 'DAMORPURP' during Spring. Age of the plant photographed is approximately 3 months from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DAMORPURP' plants grown in greenhouse in Moshav Mishmar Hashiva, Israel, under natural lighting. Measurements were taken during April of 2015. The plants were approximately 60 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia* hybrid 'DAMORPURP'.

PROPAGATION

Time to initiate roots: 10 to 14 days at approximately 20° C.

Root description: Fibrous. Tan, not accurately measured with a color chart.

PLANT

Growth habit: Mounded.

Pot size of plant described: 13 cm.

Height: About 20 cm to top of flowering plane.

Plant spread: About 45 cm.

Growth rate: Medium.

Branching characteristics: Very branched.

Length of primary lateral branches: About 22 cm.

Quantity of primary lateral branches: 8.

Characteristics of primary lateral branches:

*Form.*—Cylindrical.

*Diameter.*—About 0.2 cm.

*Color.*—RHS Yellow-Green 144B.

*Texture.*—Pubescent.

*Strength.*—Good.

Internode length: About 2 cm.

FOLIAGE

Leaf:

*Arrangement.*—Opposite.

*Quantity.*—Approximately 22 per branch.

*Average length.*—5.5 cm.

*Average width.*—2.0 cm.

*Shape of blade.*—Elliptic.

*Apex.*—Acute.

*Base.*—Acute.

*Margin.*—Entire.

*Texture of top surface.*—Velvety.

*Pubescence.*—Pubescent, both sides.

*Aspect.*—90 degrees.

*Variegation.*—Absent.

*Color.*—Young foliage upper side: RHS Yellow-Green 146 A. Young foliage under side: RHS Yellow-Green 146 B. Mature foliage upper side: RHS Yellow-Green 146 A. Mature foliage under side: RHS Yellow-Green 146 B.

*Venation.*—Type: Pinnate. Venation color upper side: RHS Yellow-Green 146 B. Venation color under side: RHS Yellow-Green 146 C.

*Petiole.*—Length: About 0.6 cm. Diameter: About 0.3 cm. Color: RHS Yellow-Green 146 C. Texture: Velvety.

FLOWER

Natural flowering season: Spring, Summer, and Autumn in Mishmar Hashiva, Israel.

Days to flowering from rooted cutting: About 30 days.

Inflorescence and flower type and habit: Axillary, single flower, salverform shape, erect habit.

Rate of flower opening: 2 to 3 days from bud to fully opened flower.

Flower longevity on plant: 3 to 6 days.

Approximate quantity of flowers per plant: About 70.

Persistent or self-cleaning: Self-cleaning.

Bud:

*Shape.*—Tubular.

*Length.*—About 4 cm.

*Diameter.*—About 0.6 cm.

*Color.*—RHS Yellow-Green 145B with stripes RHS Violet 83B.

Flower size:
*Diameter*.—About 5.5 cm.
*Length*.—About 3 cm.
*Flower tube diameter at distal end*.—About 1 cm.
*Flower tube diameter at proximal end*.—About 0.2 cm.
Petals:
*Length from throat*.—About 2.3 cm.
*Width*.—About 2.5 cm.
*Quantity*.—5.
*Texture*.—Velvety, both sides.
*Apex*.—Blunt.
*Margin*.—Entire.
*Lobing*.—Weak.
*Veins*.—Very weak, inconspicuous.
Color:
*When opening*.—Upper surface: RHS Violet-Blue N 89 B with 5 stripes, White NN 155 D. Lower surface: RHS Violet-Blue N 89 C with 5 stripes, White NN 155 D.
*Fully opened*.—Upper surface: RHS Violet N 88 A with 5 stripes, White NN 155 C. Lower surface: RHS Violet N 88 B with 5 stripes, White NN 155 C. Flower throat (inside): RHS Yellow 9C with 5 stripes, Violet N88A. Flower throat, vein: RHS Green-Yellow 1B. Flower tube (outside): RHS Green-Yellow 1C with 5 stripes, Violet 86B. Flower tube, vein: RHS Green-Yellow 1B.
*Fading*.—Petals fading to: RHS Violet N 88B with 5 stripes, White NN 155C.
Calyx/sepals:
*Quantity per flower*.—5.
*Shape*.—Linear.
*Length*.—About 2 cm.
*Width*.—About 0.2 cm.
*Apex*.—Acute.
*Base*.—Cuneate.
*Margin*.—Entire.
*Texture*.—Velvety.
*Color*.—Upper Surface: RHS Yellow-Green 146 A. Lower Surface: RHS Yellow-Green 146 B.
Peduncle: Not present.
Pedicel:
*Length*.—About 2.5 cm.
*Diameter*.—About 0.12 cm.
*Color*.—RHS Yellow-Green 146 C.
*Orientation*.—45 degrees.
Fragrance: None.

REPRODUCTIVE ORGANS

Stamens:
*Number*.—5.
*Filament length*.—About 2 cm.
Anthers:
*Length*.—About 0.2 cm.
*Shape*.—Rounded.
*Color*.—RHS Yellow-White 158B.
*Pollen*.—Color: RHS Yellow-White 158A. Quantity: Plenty.
Pistil:
*Number*.—1.
*Length*.—About 2.2 cm.
*Style*.—Length: About 1.8 cm. Color: RHS Yellow-Green 150C.
*Stigma*.—Shape: Rounded. Color: RHS Yellow-Green N144B. Ovary Color: RHS Yellow-Green 146D.

OTHER CHARACTERISTICS

Seeds and fruits: About 60 dark brown (near RHS Brown 200C), rounded seeds of about 0.5 mm diameter, per one brown (RHS Brown 200A), conical capsule.
Disease/pest resistance: Neither resistance nor susceptibility to the normal diseases and pests of *Petunia* have been observed.
Temperature tolerance: Tolerates a range between 5° C. to 40° C.

What is claimed is:

1. A new and distinct cultivar of *Petunia* plant named 'DAMORPURP' as herein illustrated and described.

* * * * *